United States Patent [19]
Alexander

[11] Patent Number: 5,593,413
[45] Date of Patent: *Jan. 14, 1997

[54] DEVICE FOR ASSISTING CHILDBIRTH

[75] Inventor: Gary E. Alexander, Baton Rouge, La.

[73] Assignee: Medisys Technologies, Inc.

[ * ] Notice: The term of this patent shall not extend beyond the expiration date of Pat. No. 5,217,467.

[21] Appl. No.: 250,054

[22] Filed: May 27, 1994

Related U.S. Application Data

[63] Continuation-in-part of Ser. No. 36,560, Mar. 25, 1993, Pat. No. 5,318,573, which is a continuation-in-part of Ser. No. 982,016, Nov. 24, 1992, Pat. No. 5,217,467, which is a continuation of Ser. No. 851,068, Mar. 13, 1992, abandoned, which is a continuation-in-part of Ser. No. 522,592, May 14, 1990, Pat. No. 5,122,148.

[51] Int. Cl.$^6$ ............................ A61B 17/42; A61B 17/44
[52] U.S. Cl. ........................ 606/122; 606/119; 606/121
[58] Field of Search ................................ 606/122, 119, 606/121, 1

[56] References Cited

U.S. PATENT DOCUMENTS

| | | |
|---|---|---|
| 1,782,814 | 11/1930 | Froehlich ............................ 606/122 |
| 3,550,595 | 12/1970 | Laufe ................................. 128/323 |
| 3,605,748 | 9/1971 | Salinas-Benavides ................. 128/323 |
| 3,665,925 | 5/1972 | Dersookian ......................... 128/323 |
| 3,785,381 | 1/1974 | Lower ................................ 128/323 |
| 3,789,849 | 2/1974 | Laufe et al. ....................... 128/323 |
| 3,794,044 | 2/1974 | Vennard .............................. 128/352 |
| 4,875,482 | 10/1989 | Hariri et al. ..................... 606/122 |
| 5,122,148 | 6/1992 | Alexander .......................... 606/122 |
| 5,207,687 | 5/1993 | Bernon .............................. 606/119 |
| 5,217,467 | 6/1993 | Alexander .......................... 606/122 |
| 5,318,573 | 6/1994 | Alexander .......................... 606/1 |

FOREIGN PATENT DOCUMENTS 2925386 1/1981 Germany ............................. 606/122

Primary Examiner—Robert A. Hafer
Assistant Examiner—Benjamin Koo
Attorney, Agent, or Firm—Roy, Kiesel & Tucker

[57] ABSTRACT

A device to assist in removing a fetus from a woman's birth canal during childbirth is provided. The device includes a pliable, elongated member open at at least one end to fit over the head of the fetus, insertion means for positioning the elongated member over the head of the fetus, and restricting means attached at that one end of the elongated member to decrease the size of the opening at the one end. The elongated member is constructed so that as the elongated member is pulled from the other end, the elongated member will axially grip the head of the fetus.

11 Claims, 13 Drawing Sheets

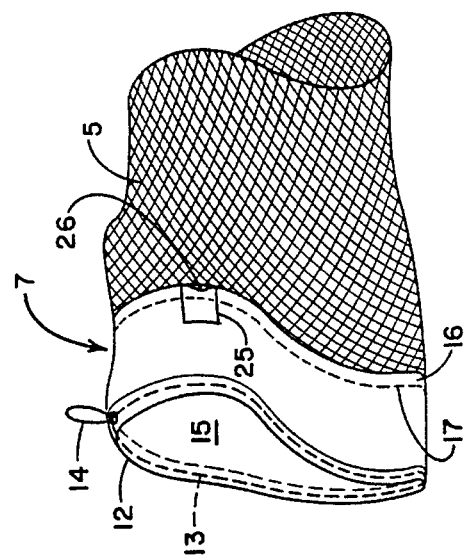
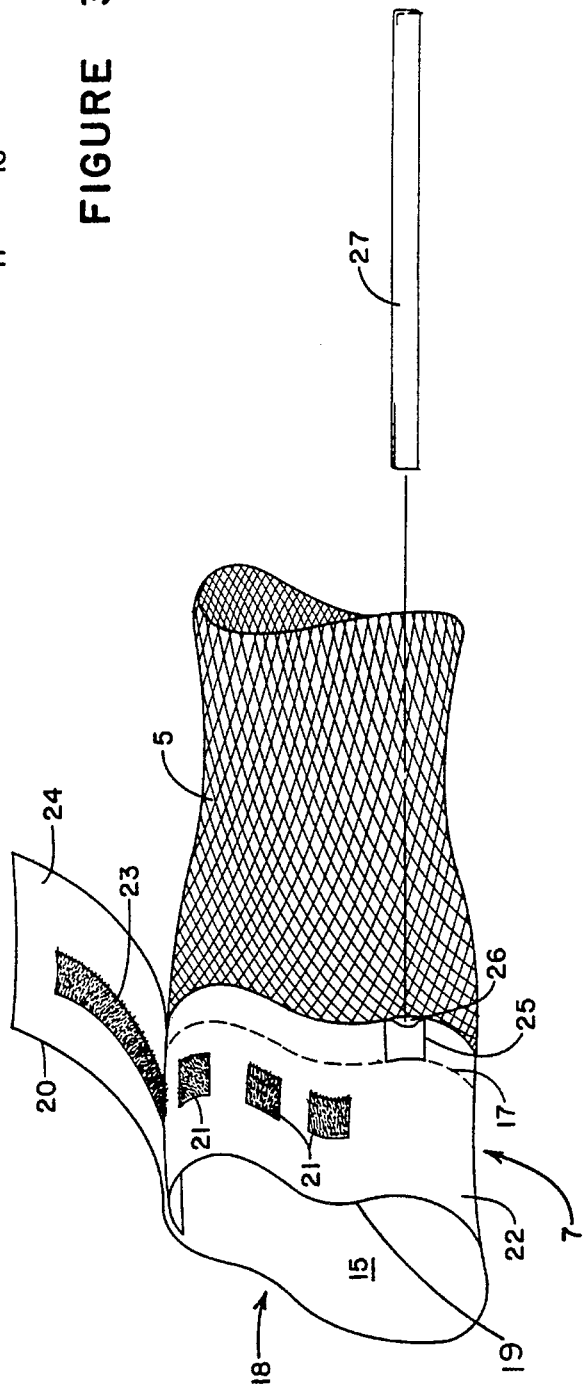
FIGURE 3
FIGURE 4

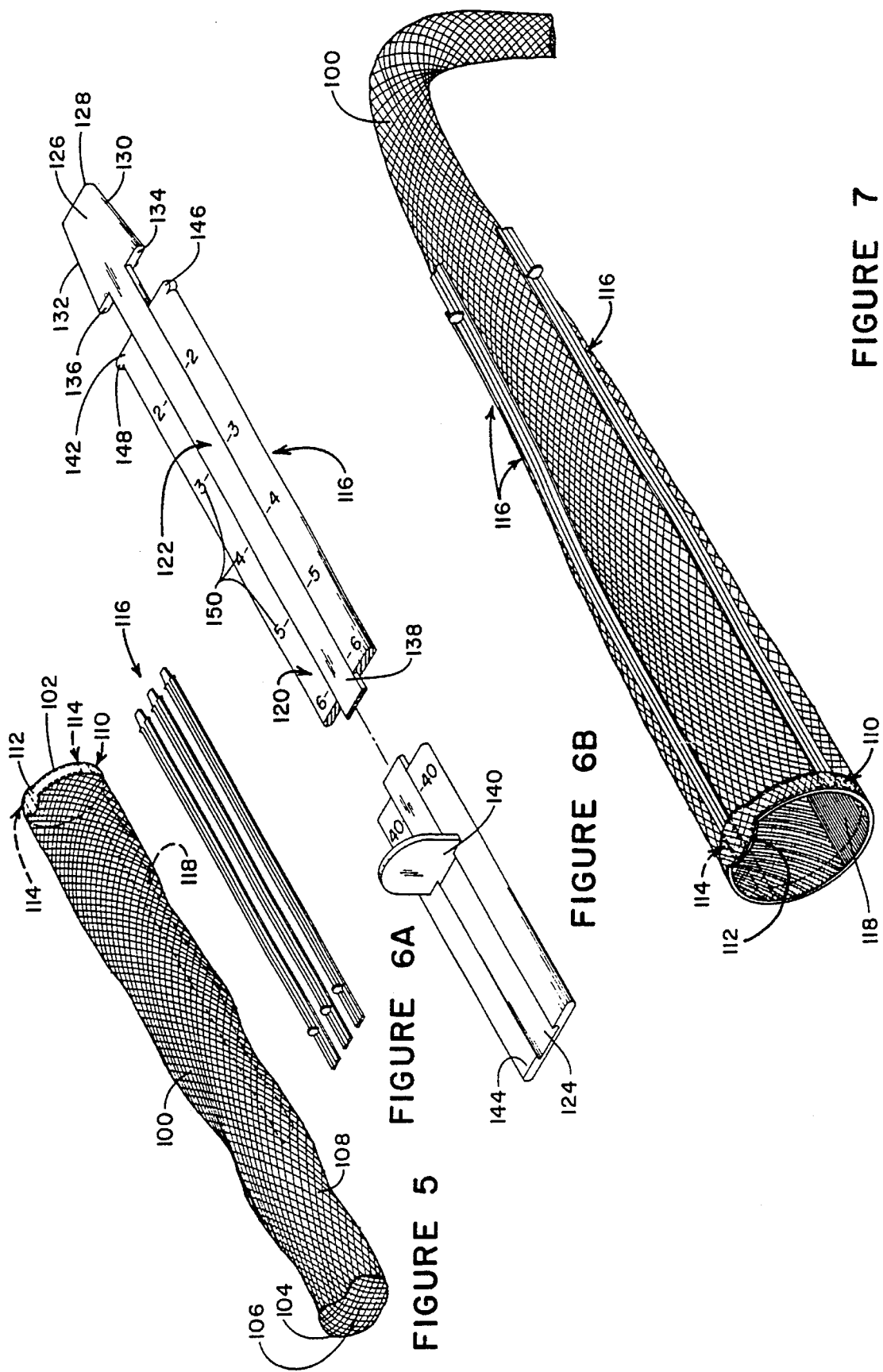

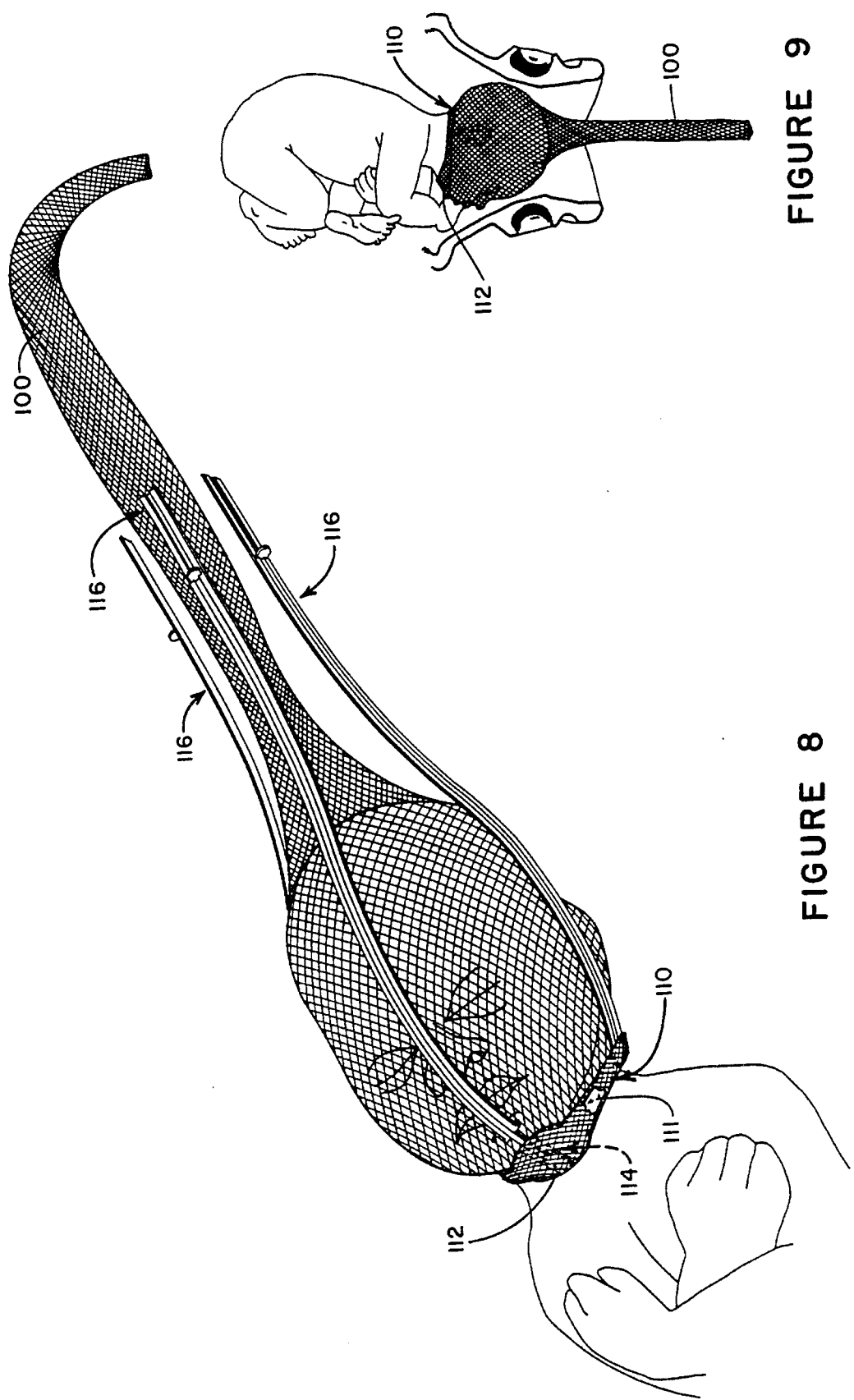

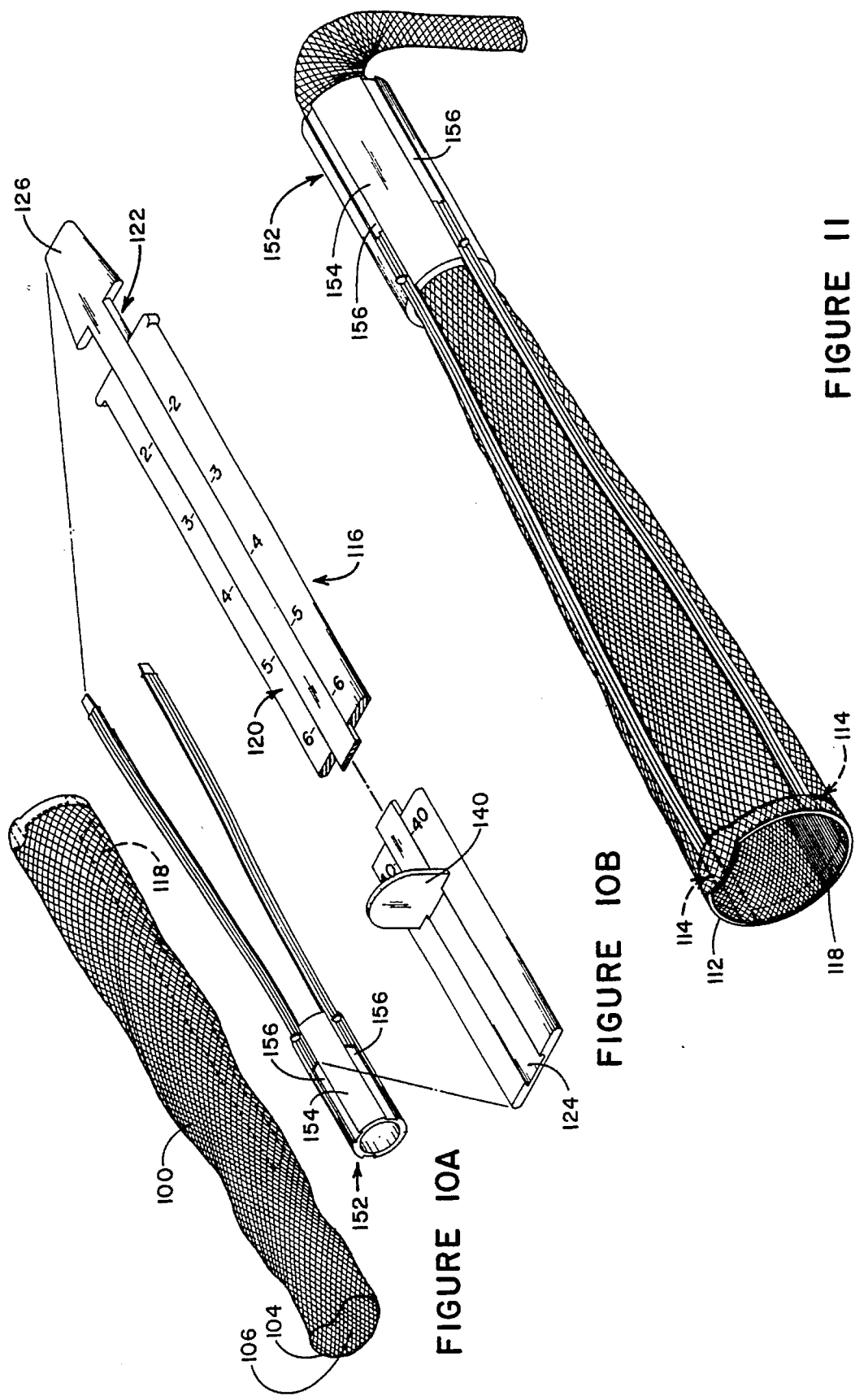

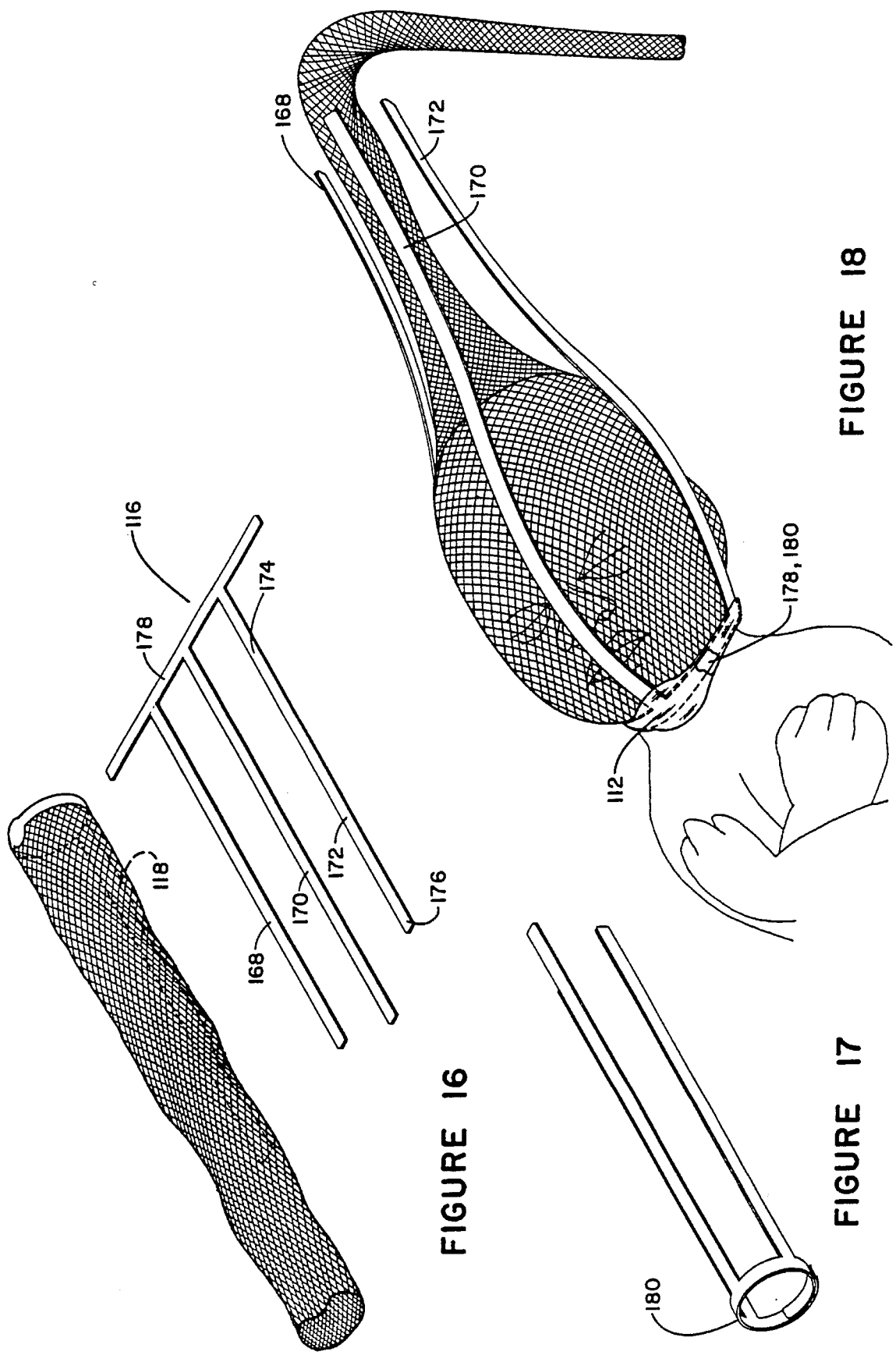

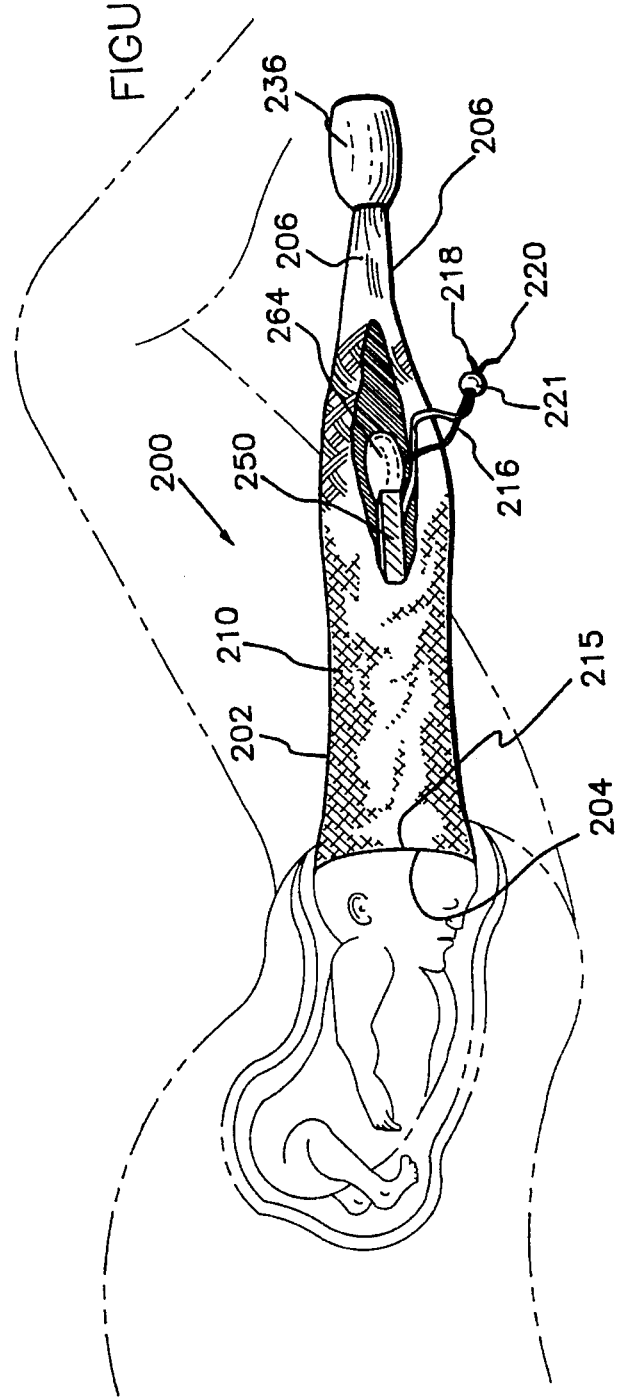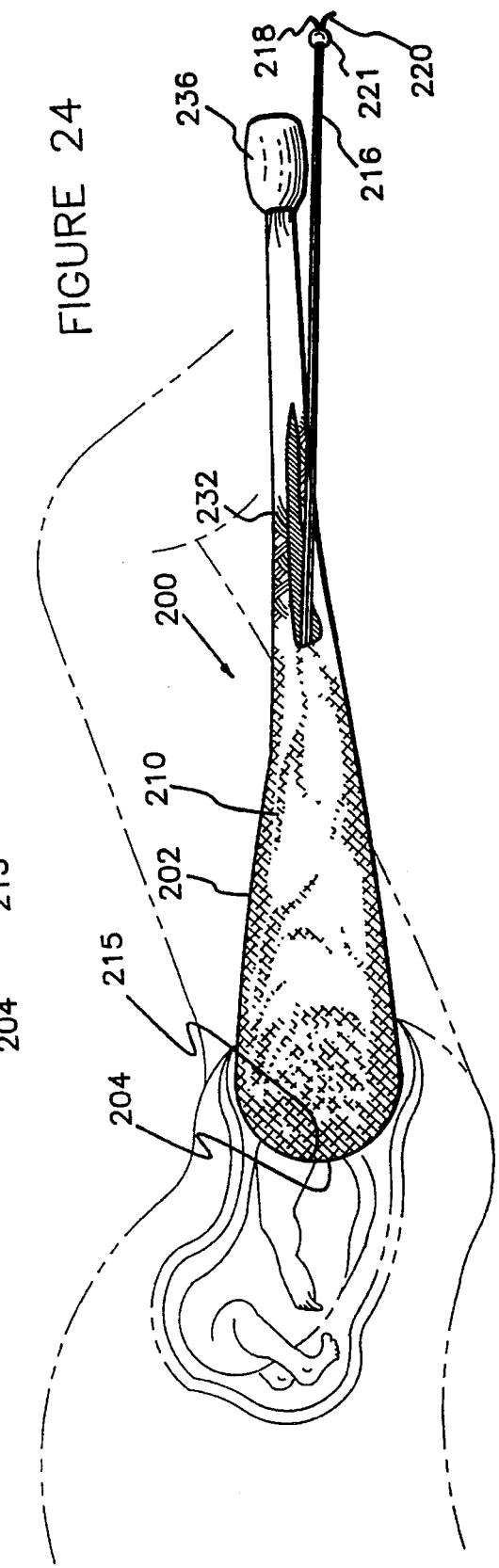

DEVICE FOR ASSISTING CHILDBIRTH

This is a continuation-in-part application of a U.S. patent application Ser. No. 08/036,560, filed on Mar. 25, 1993, now U.S. Pat. No. 5,318,573 which is a continuation-in-part application of U.S. patent application Ser. No. 07/982,016, filed on Nov. 24, 1992, now U.S. Pat. No. 5,217,467, which was a file wrapper continuing application of U.S. patent application Ser. No. 07/851,068, filed on Mar. 13, 1992 (now abandoned), which was a continuation-in-part application of U.S. patent application Ser. No. 07/522,592, filed on May 14, 1990, now U.S. Pat. No. 5,122,148.

BACKGROUND OF THE INVENTION

1. Field of the Invention

This invention relates in general to obstetric devices, and more particular to devices useful in removing the fetus during vaginal delivery.

2. Prior Art

Today's state of the art obstetrics utilizes various procedures to assist in instances of difficult vaginal deliveries. These procedures basically fall into three categories: version, Caesarian and forceps assisted delivery. In the case of severe cephalo-pelvic disproportion, placenta previa, vaso previa, and other contraindications to vaginal delivery, the "C-Section," whether classic or low transverse, remains the mainstay procedure. However, it has long been recognized that to the extent that C-Section deliveries can be successfully avoided, statistical maternal and fetal benefits will be realized. Even the non-difficult vaginal delivery can benefit from non-traumatic assists.

Many problems may develop during delivery which require assistance from the attending obstetrician to successfully remove the baby from the birth canal. One such problem results from the presenting part of the baby, usually its head, descending too slowly. This is particularly true in the case of the primigravida mother. Even with a completely dilated and effaced cervix, and an adequate pelvis, a fetus might refuse to descend beyond station "+1", especially when the mother is suffering from contraction exhaustion. This can remain a problem even with an assist from administration of oxytocin (Pitocin). This problem is frequently exacerbated by anesthesia, particularly in the instance of epidural anesthesia which frequently produces induced non-beneficial partial atony of the engaged and dedicated muscles. Such partial atony frequently results in non-beneficial, and sometimes hazardous, prolongation of labor. Station "+1" is considered mid-pelvis and in the usual case is considered too high for a forceps assisted delivery. The risks to the fetus with forceps application at this level are extreme. Forceps cannot be safely used until the presenting part is at least at station "+2", and preferably between stations "+2" and "+3", which is the floor of the perineum.

Modern obstetrics has not developed an alternative to the use of forceps when an assisted natural delivery is indicated, such as when the fetus is consistently exhibiting late decelerations of heartbeat following contractions or is exhibiting non-variability of the baseline heartbeat rate. Obstetrical forceps are typically, in their various types, two-bladed instruments which are blindly inserted one blade at a time in a hopefully temporal-cheek position and then articulated together before assisting traction is applied. Actual traction is exerted slightly below or underneath the mandible. Traction applied with forceps is point concentrated and slippage of the forceps is increased because of natural lubrication, refusal of the fetal skull to conform to existing forceps design, and other known myriad of variables that vary from one fetus-to-pelvis physical relationship to another.

Even proper positioning of the forceps can result in harm to the fetus. For example, in instances of minimal cephalopelvic disproportion, the insertion of one blade of the forceps can exacerbate any slight deficiency in birth canal adequacy. In addition the softness, or pliability, of the fetal skull, coupled with the existence of sutures which separate the plates of the skull, render the skull susceptible to trauma associated with metal forceps assisted deliveries.

The problems associated with forceps assisted deliveries are well known, and many attempts have been made to improve forceps design. Examples of the current state of the art in forceps design can be seen in the following patents: U.S. Pat. No. 3,550,595 entitled "Obstetrical Forceps" and issued on Dec. 29, 1970 to Leonard E. Laufe; U.S. Pat. No. 3,605,748 entitled "Obstetrical Forceps" and issued on Sep. 20, 1971 to Hector Salinas-Benavides; U.S. Pat. No. 3,665,925 entitled "Obstetrical Forceps" and issued on May 30, 1972 to Hamo M. Dersookian; U.S. Pat. No. 3,785,381 entitled "Pressure Sensing Obstetrical Forceps" and issued on Jan. 15, 1974 to Brenton R. Lower et al; U.S. Pat. No. 3,789,849 entitled "Obstetrical Forceps" and issued on Feb. 5, 1974 to Leonard E. Laufe et al; and U.S. Pat. No. 3,794,044 entitled "Delivery Forceps" and issued on Feb. 26, 1974 to William O. Vennard.

Despite the long felt need and the large amount of time and effort spent to develop an alternative to forceps, the only assisting device developed which has seen some application is a vacuum extractor. Because the vacuum extractor presents its own set of clinical problems and risks, its use is limited and it has not served to supplant the use of forceps.

OBJECTS AND SUMMARY OF THE INVENTION

It is therefore an object of this invention to provide an assisting device for childbirth which can safely perform substantially all of the functions of forceps and vacuum extractors without the risks inherent in the use of these devices.

Another object of this invention is to provide an assisting device for childbirth that is easy to use and reduces the risk of injury to the fetus during childbirth.

Still another object of this invention is to provide an assisting device for childbirth that can be quickly applied to the head of the fetus by the attending obstetrician.

Still another object of this invention is to provide an assisting device for childbirth that can be quickly applied to the lower portion of the fetus by the attending obstetrician in the case of a breech birth.

Still other objects and advantages of this invention shall become apparent from the ensuing descriptions of the invention.

BRIEF DESCRIPTION OF THE DRAWINGS

FIG. 3 is an enlarged view of one embodiment of the collar means forming part of this invention.

FIG. 4 is an enlarged view of another embodiment of the collar means forming part of this invention.

FIG. 5 is a three dimensional view of another embodiment of this invention.

FIG. 6A is a three dimensional view of one embodiment of the insertion means.

FIG. 6B is an enlarged view of the insertion means seen in FIG. 6A.

FIG. 7 is a three dimensional view of one embodiment of this invention which utilizes the insertion means of FIGS. 6A and 6B.

FIG. 8 is a three dimensional view of a fetus to which the embodiment depicted in FIG. 7 has been attached.

FIG. 9 is a cut-away view of a fetus positioned for vaginal delivery utilizing another embodiment of the invention.

FIG. 10A is a three dimensional view of one embodiment of the wand holding means of the invention.

FIG. 10B is an enlarged view of one embodiment of the insertion means.

FIG. 11 is another three dimensional view of one embodiment of the invention utilizing the wand holding means.

FIG. 16 depicts an alternate embodiment of the invention.

FIG. 17 is another view of the embodiment seen in FIG. 16.

FIG. 18 is a three dimensional view of the embodiment seen in FIG. 17 attached to the head of a fetus.

FIG. 23 is an illustrative view of the embodiment of FIG. 20 being placed about the head of the fetus.

FIG. 24 is an illustrative view of the embodiment of FIG. 20 as the device is in traction.

PREFERRED EMBODIMENTS OF THE INVENTION

Figure 1:
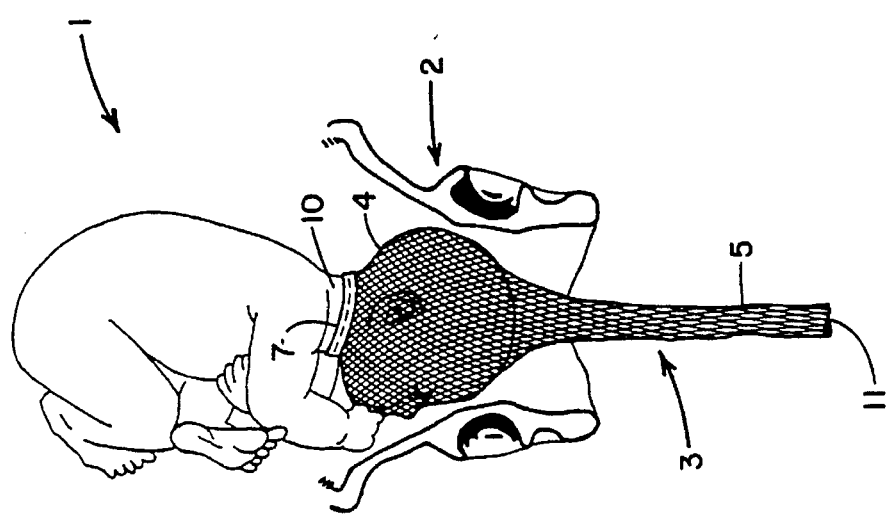
FIG. 1 is cutaway view of a fetus positioned for vaginal delivery to which has been attached one embodiment of this invention.

Like numbers in the various figures refer to like components from the specification. Referring now to FIG. 1 which depicts one embodiment of the present invention, a fetus, generally denoted by numeral 1, is depicted positioned in a cutaway of a portion of a woman's birth canal 2 having the childbirth assist device 3 attached to its head 4 and trailing outside of the vagina area of the birth canal 2.

Figure 2:
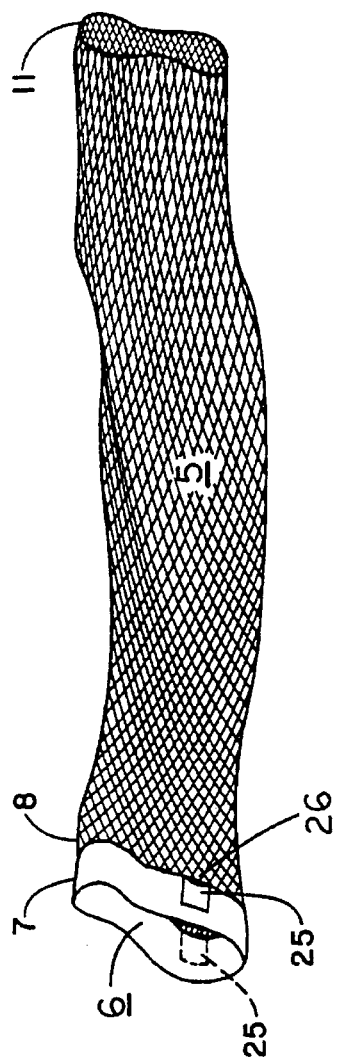
FIG. 2 is a three dimensional view of one embodiment of this invention.

In its broadest context as shown in FIG. 2, the device 3 comprises an elongated sock-like member 5 open at both ends not only to allow a physician to fit his hand and arm in passageway 6 of member 5 for rotational purposes, but also to allow the head 4 to fit into passageway 6. In addition device 3 comprises a collar 7 attached at one end 8 of member 5 which can be adjusted to restrict the size of opening 9 formed at end 8.

In one embodiment, member 5 is constructed from material having some elasticity characteristics, and more preferably from a material selected from a group consisting of natural fibers or man-made plastic fibers. Natural fibers could include cotton, linen and silk. Plastic fibers could include nylon, dacron and rayon. Preferably the degree of elasticity should be at least to a degree such that the material would begin to stretch before the pulling force exceeded a predetermined amount. That amount would depend on the stage of development of the fetus, as well as other known factors. The degree of elasticity is preferably set so the pulling force is less than that which would harm the fetus. Member 5 is also preferably pliable so that it can be shaped and easily moved in position about head 4. In another preferred embodiment the material will be constructed from a mesh material, the size of the mesh would preferably be sufficiently small enough to reduce chances of non-beneficial oral ingestion of toxic meconium by the fetus. In still another preferred embodiment the fabrics would be sterilized and lubricated with K-Y jelly to reduce or prevent the fabric from absorbing the natural lubricants within the womb. K-Y jelly is a brand name for a product sold by Johnson & Johnson.

The member 5, which in one embodiment will be constructed of the aforementioned mesh material, will comprise an angular mesh as seen at 5 of FIG. 4. Once the member 5 has been placed in position over the head of the fetus, this angular mesh will impart a uniform distribution of forces, as in the manner of the Chinese handcuff, as the member 5 is pulled in a linear direction, with respect to the passageway 6. In other words, each area of the head of the fetus which is in contact with the mesh of member 5 will have exerted against it an axial gripping force created by the diminishment of size of the angular mesh secondary to traction; thus, as the member 5 is pulled, all of the pulling force will be distributed across the area which is in contact with the head of the fetus once axial gripping of the head of the fetus has been initiated. Also, in one embodiment, the angular mesh is constructed of a synthetic or natural fiber. The fiber can be round or elliptical in cross-section and be mono-filament or bi-filament fibers.

In the embodiment shown in FIG. 2, collar 7 is constructed of an elastic material which can be stretched to fit about head 4 and then will contract to an extent to fit loosely about the neck area 10 of the fetus 1. In this manner collar 7 will not choke the fetus 1, but also will not easily slip over the head 4 when the physician pulls on end 11 of member 5 during the delivery process as described below.

In another embodiment as shown in FIG. 3, collar 7 is constructed from a pliable material wherein one edge section 12 has been folded over and stitched to itself to form a drawstring sleeve 13 in which drawstring 14 has been placed. When drawstring 14 is pulled opening 15 is restricted. The other edge section 16 of collar 7 is stitched or otherwise connected to member 5 along line 17.

In a third embodiment as shown in FIG. 4, collar 7 is constructed of a strip 18 of pliable material having one section 19 stitched or otherwise connected substantially about the perimeter of end 18, and having another section 20 that can extend over a portion of the first section 19. Strips 21 of Velcro or similar material are attached to side 22 of section 19 in a position to be alignable with at least a portion of the strips 23 of Velcro or similar material attached to side 24 of section 20. Velcro is a registered trademark of VELCRO INDUSTRIES, B.V. (NETHERLANDS CORPORATION) identifying hook and loop fastener systems. The size of opening 15 can be adjusted by changing the alignment of the strips 21 and 23. Opening size is then maintained by contacting the overlapping sections of the strips to one another.

In the embodiment as illustrated in FIGS. 2–4, collar 7 is provided with one or more pockets, preferably two or more, formed by a piece 25 of fabric that is attached on three sides to collar 7 to form an opening 26 facing toward member 5. The opening 26 will be large enough so that one end of wand 27 can be inserted through the opening. Wand 27 is preferably constructed from a flexible material, such as plastic, that will allow it to conform to the shape of the fetus' head, yet rigid enough to allow it to be used to push collar 7 around the fetus' head when positioning device 3.

Referring to FIG. 5, another embodiment of the present invention is depicted. The elongated member 100 has a first end 102 and a second end 104, with a passageway 106 defined therein. The member is constructed of the angular mesh material 108, as previously described. The collar means 110 is constructed of pliable material and is similar in design to the collar 7 in that collar 110 is connected to the first end 102 of the elongated member 100, so that the first end 102 encircles the neck of the fetus. The collar means 110 will have an elastic band 111, as seen in FIG. 8, sewn into the hem of the collar and sized to rest at a diameter sufficient to preclude carotid or larynx compression and to expand to a diameter sufficient to permit application over the largest portion of the fetal skull.

The collar means 110 will also contain a widened below chin segment 112, which is also illustrated in FIG. 7. The chin segment 112 is generally a protuberance on the collar means 110 which is adapted so that the chin of the fetus can be abutted adjacent thereto when the elongated member 100 is being pulled during childbirth. The collar means 110 will also comprise pocket means 114, similar to the aforementioned pockets 25, for receiving the wand or wands 116, which are also referred to as insertion means 116, as seen in FIG. 6A.

The elongated member 100 can also posteriorly contain a linear mesh segment 118 which is attached to the first end 102 and is best seen in FIG. 7. The linear mesh segment 118 will exhibit enhanced tensile properties so that during delivery, the fetus' skull may be tilted in a vertical plane relative to the sternum by applying traction to the linear mesh segment 114 to achieve increased flexion.

Figure 19:
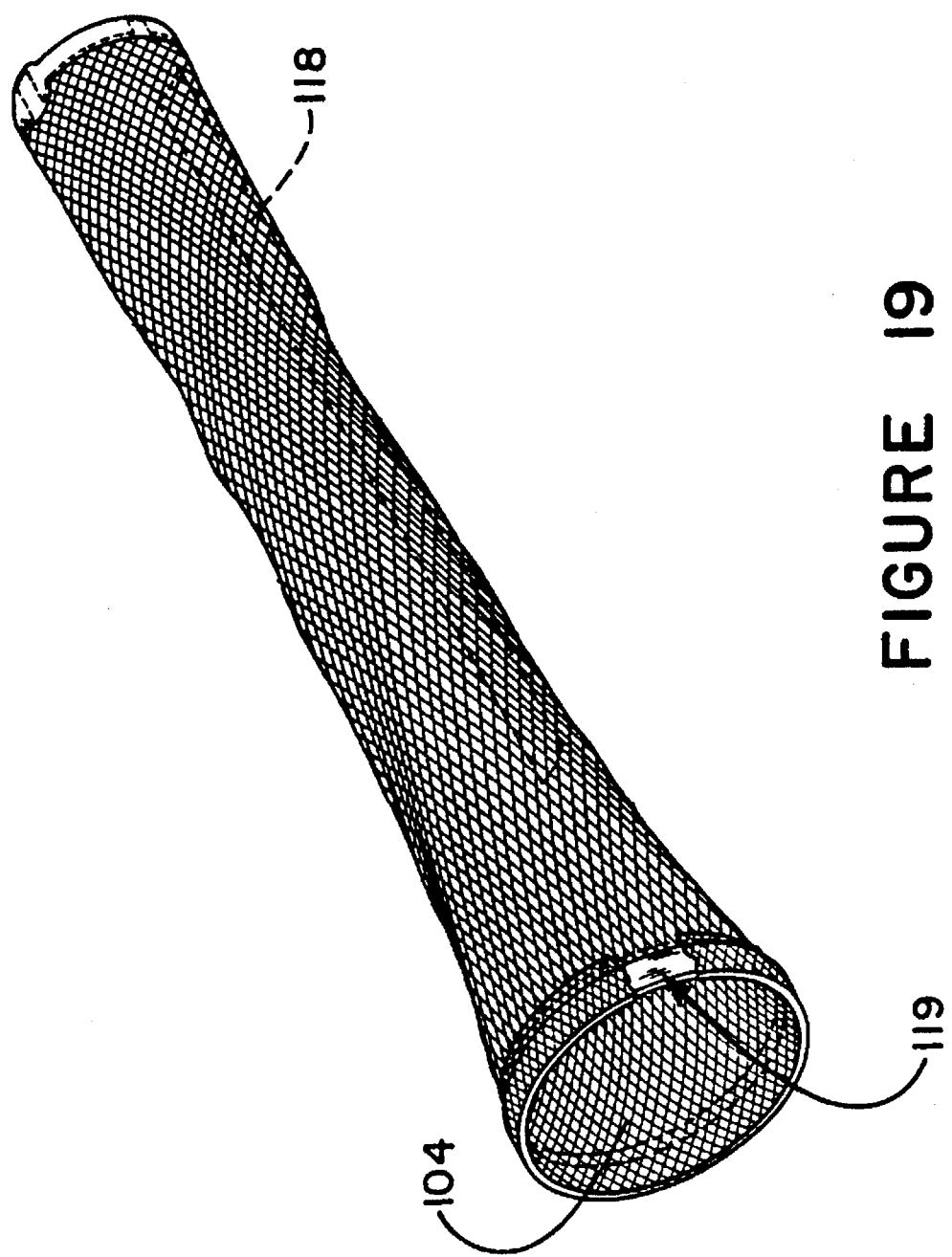
FIG. 19 is a three dimensional view of another embodiment of the invention.

As seen in FIG. 19, the second end 104 can contain an access means 119, which is a rigid, plastic ring of an internal diameter equal to or slightly larger than the internal diameter of the passageway 106. The access means will permit the immediate access through the cylinder to the fetal skull for usual and necessary obstetrical procedures.

Referring to FIGS. 6A and 6B, one embodiment of the insertion means will now be described. The insertion means 116, or wand 27 as referred to earlier in this application, is provided for inserting the collar means 110 over the head of the fetus. Insertion means 116, as seen in FIGS. 6A and 6B, will each have a first and second member 120, and 122. The second member 122 will overlay the first member 120 in the slotted groove 124 of member 120.

Member 120 will have a first end wedge section 126, with wedge section 126 having a first surface 128 which extends to angled shoulders 130 and 132. Shoulder 130 terminates at the back surface 134 and shoulder 132 terminates at the back surface 136. Both surfaces 134 and 136 extend to the elongated segment 138, with the elongated segment extending to the perpendicular segment 140, also known as the thumb tab.

The elongated segment 138 is slidably disposed within the groove 124 of the first member 120 so that the segment may be moved outward or inward in a telescopic fashion. Thus, if the operator is holding first member 120, and exerts a force on the thumb tab 140, the second member will be moved away relative to the first member 120.

First member 120 will have a first end 142 and second end 144, with first end 142 containing ridges 146 and 148. Ridges 146 and 148 will be sized so that as the ridges are placed within the pockets 112, the ridges 146 and 148 engage the pocket with some mechanical restriction. First member 120 will also have defined thereon graduations 150, marked in centimeters.

Referring now to FIG. 7, the insertion means 116 have been inserted into the pocket means 114 before the apparatus is attached to the fetus. In this position, the ridges 148 and 146 are fitted into pocket means 114 with some mechanical restriction so that the ridges do not easily slip out of the pockets during positioning of the apparatus. In FIG. 8, the invention is attached to the head of the fetus. Collar means 110 has been positioned around the neck of the infant and the chin segment 112 has been placed beneath the mandible area using insertion means 116. The elastic band 111 of the collar means 110 will, therefore, cause the collar to surround the neck so that the elongated member 100 does not slip off.

After the proper position has been obtained about the fetus, the insertion means 116 can be removed from the pockets 114 as seen in FIG. 8. This will entail the physician having to hold member 120, then begin pushing second member 122 by pushing on the thumb tab 140 in a direction such that surface 128 is constrained against the pocket means 114. This will cause wedge section 126 to continue to act against the pocket means 114 and thereby cause the collar means 110 to move, but because the member 120 is being held stationary, the ridges 146 and 148 will be slipped out of the pocket 112. Conversely, the physician can hold the thumb tab 140 stationary, and pull on the first member 120 thereby disengaging the ridges 146 and 148 from the pockets.

FIG. 9 shows a cut-away view of the fetus in the birth canal after placement of the collar means 110 in the position for removal of the fetus. As can be seen from this view, the chin segment 112 is centered below the mandible. As noted earlier, as the elongated member 100 is pulled by the operator of the device, which in most cases is a medical doctor, the axial gripping forces of the mesh will distribute the pulling forces to all areas of the mesh which have been expanded by the head of the fetus.

Referring to FIG. 10A and 10B, wand holding means 152 is shown which may be used for holding and placing the aforementioned insertion means 116 into the pocket means 114. Wand holding means 152 comprises generally a tubular cylinder 154 which has an internal diameter roughly the size of the passageway 106. The cylinder 154 will contain a plurality of slots 156 which will have fitted therein the first member 120 of the insertion means 116. In particular, second end 122 will be inserted into one of the slots 156. In the preferred embodiment of wand holding means 152, there will be three slots, such that three wands 116 can be attached to wand holding means 152.

As seen in FIG. 11, wand holding means 152 has been attached to the elongated member 100 by placing the second end 144 of insertion means 116 into the slots 156, and by having the wedge section 126 of the second member 122 engaged with the pocket means 114. As seen in FIG. 11, the apparatus, which includes wand holding means 152 containing the insertion means 116, is now available for placement over the head of the fetus.

Figure 12:
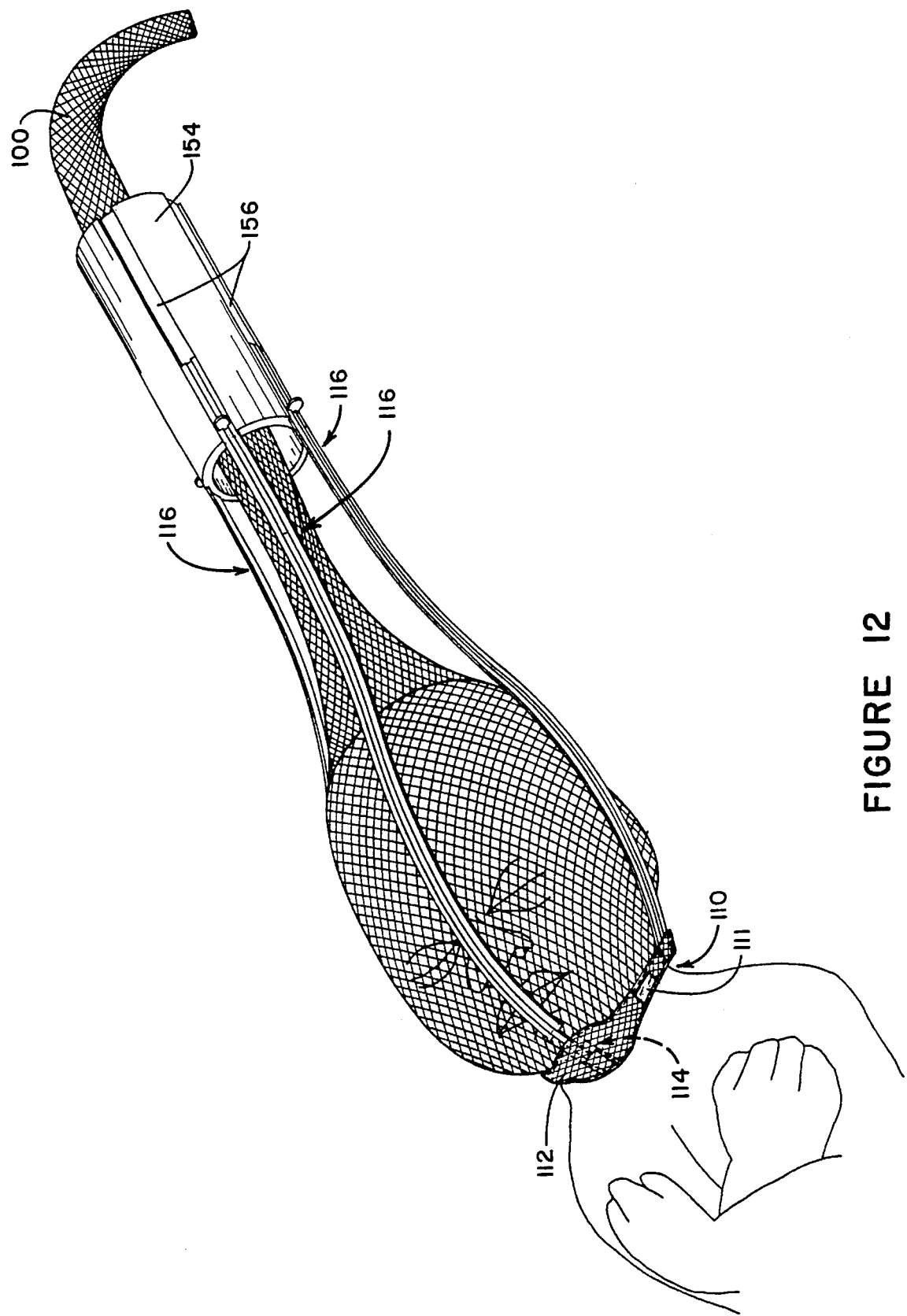
FIG. 12 is a three dimensional view of the wand holding means being utilized to position one embodiment of the invention over the head of a fetus.

In order to remove wand holding means 152, disengagement of the wands 116 from the pocket means is accomplished as previously discussed. FIG. 12 shows the position of wand holding means 152 after the apparatus has been placed over the head of the fetus and removal of the insertion means has begun. FIG. 12 also shows the elastic band 111 of the collar means 110.

Figure 13:
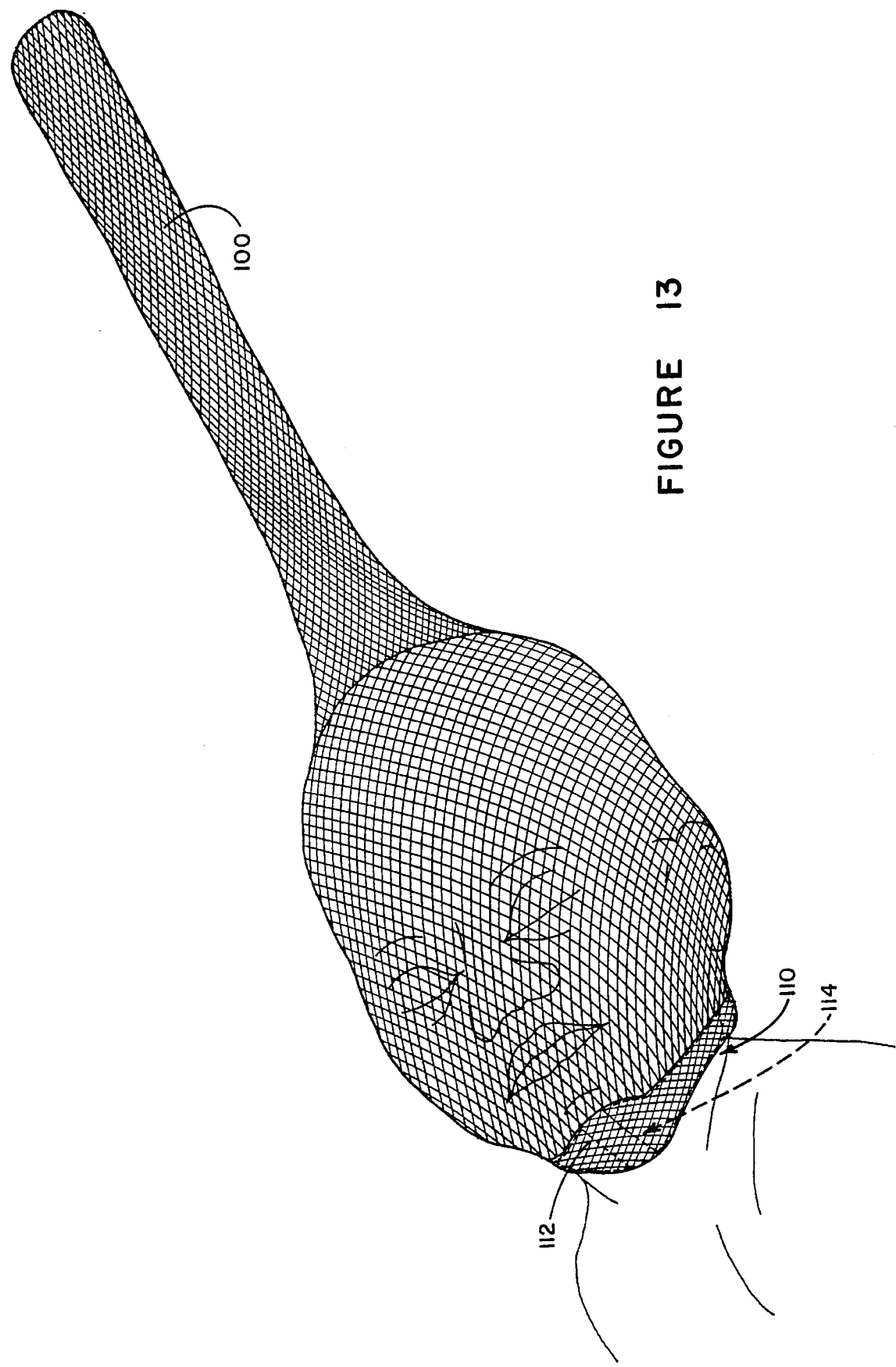
FIG. 13 is a three dimensional view of one embodiment of the invention attached to the head of a fetus.

Turning to FIG. 13, the elongated member 100, along with the collar means 110 and chin segment 112, is shown after the insertion means 116 have been removed. As can be seen, the angular mesh has been expanded by the head of the fetus so that the previously described axial gripping force will be applied once the doctor has exerted a lateral pull on member 100 to assist in the removal of the fetus from the birth canal.

Figures 14A, 14B, 15:
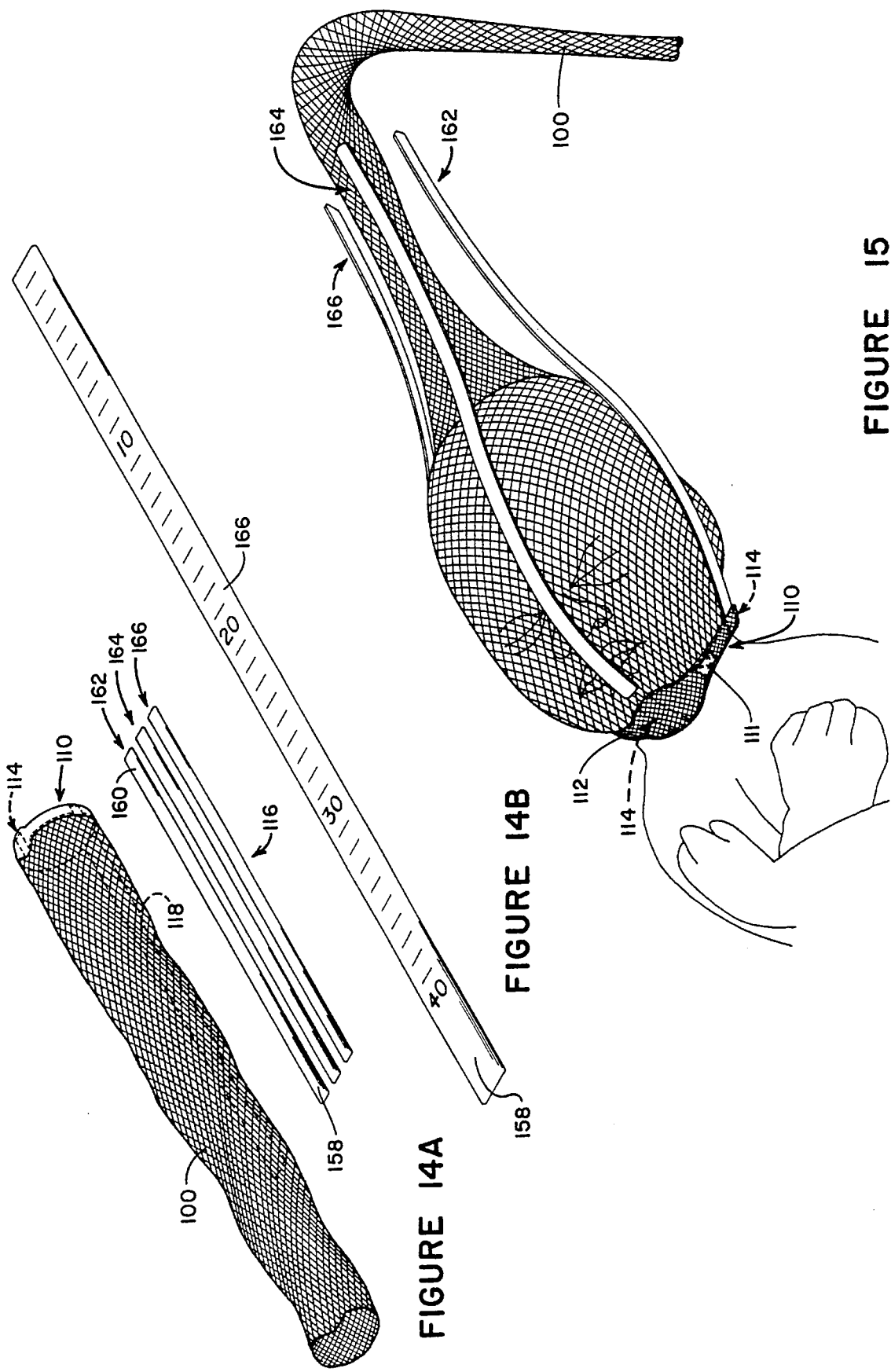
FIG. 14A depicts a plurality of the insertion means utilized with the embodiment of FIG. 13.
FIG. 14B is an enlarged view of one of the insertion means as seen in FIG. 14A.
FIG. 15 is a three dimensional view of the embodiment depicted in FIG. 13 attached to the head of a fetus.

Referring now to FIGS. 14A, 14B, and 15, another embodiment of the present invention will be discussed. The insertion means 116 consist of one or more single, flat, one-piece flexible wands each with a first end 158 and second end 160. In the embodiments of FIGS. 14A, 14B and 15, three flexible wands will be employed, 162, 164 and 166. The single wands, 162, 164 and 166, will have already been placed within the pocket means 114 which are disposed about the collar means 110 before the apparatus is placed over the head of the fetus.

FIG. 14B shows an enlarged view of the wand 166, with graduations in centimeters. The first end 158 will fit with some mechanical resistance into the pocket means 114, as can also be seen in FIG. 15. Thus, as shown in FIG. 15, the wands 162, 164, and 166 are positioned within the pocket means 114 of collar means 110. The first end 158 of wand 164 is illustrated as being pulled away from the collar means 110. In other words, the wand 164 has been pushed downward into the proper below mandible position by manipulating the wand downward. Next, wands 162 and 166 are manipulated, and once the proper position is reached, the wands 162, 164, and 166 can be removed by pulling the wands away from the pocket means 114, which is shown by the relative position of wand 164 to the collar means 110.

FIG. 16 depicts another embodiment of the insertion means 116. In this embodiment, the insertions means 116 consist of three flat, elongated wands 168, 170 and 172. Each of these wands will have a first end 174 and a second end 176, with the first end 174 of the wands 168, 170 and 172 being joined to a perpendicular member 178 which forms wand collar 180, as seen in FIG. 17. In this embodiment, the perpendicular member 178 will be fitted into a folded latex hem of the woven mesh cylinder. The internal diameter of wand collar 180 at rest will be sufficient to preclude compression of the carotids or of the larynx and with an expansion diameter sufficient to permit application over the fetal skull. FIG. 18 shows the member 178 in place, as the member 178 has been folded to form wand collar 180.

Figure 20:
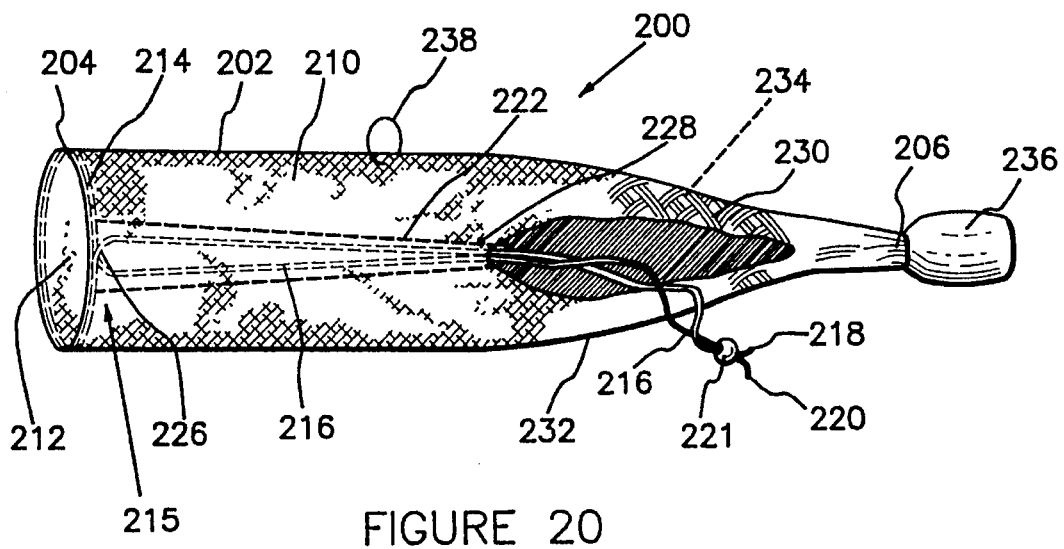
FIG. 20 is a three dimensional view of the preferred embodiment of the invention.
Figures 22A, 22B:
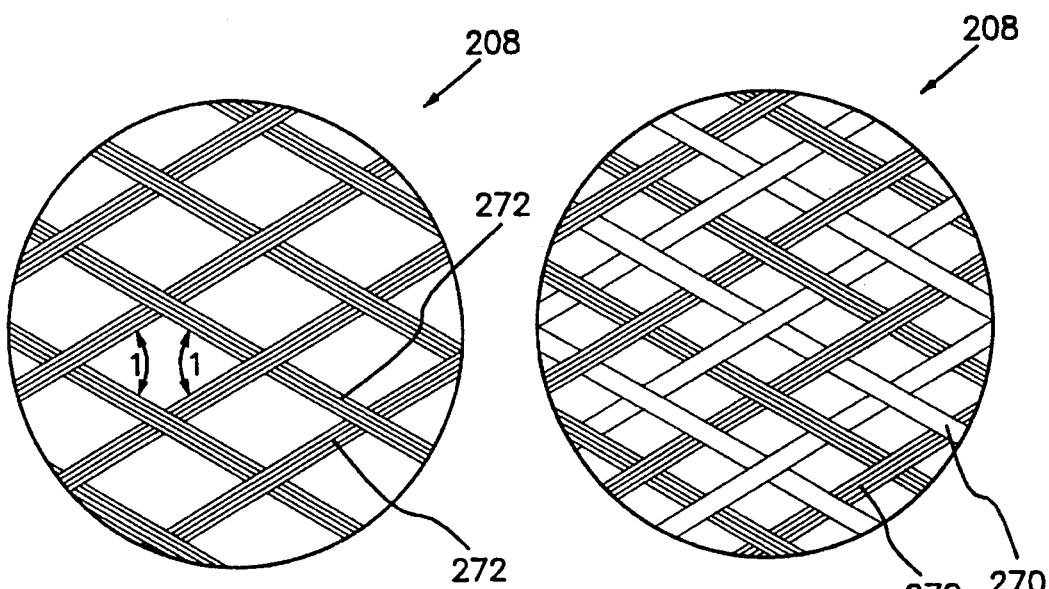
FIG. 22A and 22B are enlarged views of segments of the material which can be used in the embodiment depicted in FIG. 20.

Referring to FIG. 20, the preferred embodiment of this invention will now be described. The device for assisting childbirth, seen generally at 200, comprises elongated member 202 having a passageway, elongated member 202 including an open first end 204 and a second end 206. Elongated member 202 will be formed of braid material 208 that is depicted in FIGS. 22A and 22B and will be more fully described later in this application.

Elongated member 202 will have a first outer layer 210 and a second inner layer 212. As depicted in FIG. 20, the preferred way to obtain this outer 210 and inner 212 layered elongated member 202 is to extrude a continuous cylindrical member, and then, fold the cylindrical member so that a first outer layer 210 and a second inner layer 212 are formed. One could terminate braid material 208 by cutting braid material at open first end 204 and sewing or binding together the fibers. However, it is preferred to terminate braid material 208 by folding braid material 208 to form a two-layered member because this embodiment will enhance the axial gripping aspects of braid material 208 and will be easier to manufacture.

Once the cylindrical member has been folded over, open first end 204 is formed. Restricting means 215 for tightening said open first end about the neck and head of the fetus is generally located at open first end 204. Restricting means 215 includes drawstring sleeve 214, which can be an enveloping structure such as a nylon tube that will contain drawstring 216. Although in the embodiment depicted, drawstring sleeve is a nylon tube, one could route drawstring 216 through loops attached to open first end 204, could weave drawstring 204 through the braid material, or could use any other means capable of causing drawstring 216 to cooperate with open first end 204 and tighten open first end 204 around the neck and head of the fetus when drawstring 216 is pulled.

Drawstring 216 has first end 218 and second end 220 which are held together by fastener 221. As can be seen in FIG. 20, drawstring 216 is looped around open first end 204 within drawstring sleeve 214 such that the looped portion of drawstring 216 constitutes part of restricting means 215. Thus, as the drawstring 216 is pulled, generally from the fastener 221, the looped portion of the drawstring 216 will decrease in size, which in turn will cause the size of the opening at open first end 204 to decrease.

Figure 21:
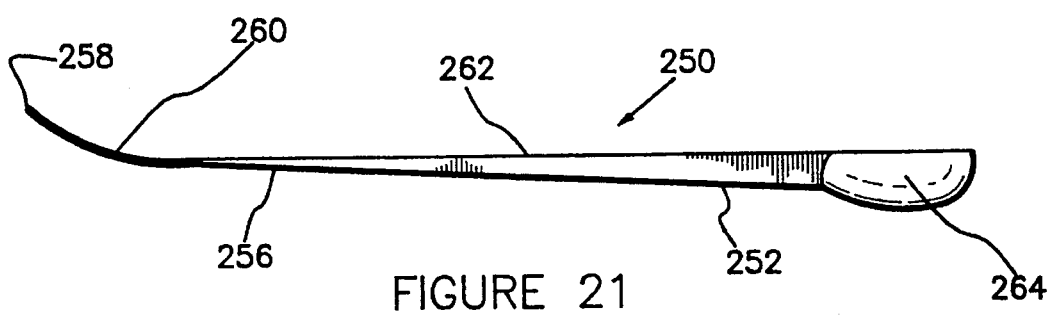
FIG. 21 is a two dimensional view of the insertion wand member used with the preferred embodiment illustrated in FIG. 20.

A sheath 222 which is positioned between the outer layer 212 and the inner layer 212 is also provided. The drawstring 216 can be held within the sheath 222 as seen in FIG. 20. A second sheath positioned approximately 180 degrees from the first sheath 222 may also be provided but has not been shown. The sheath is generally an elongated nylon pocket member that is adapted to receive the insertion wand member 250 as seen in FIG. 21, and as will be described in further detail.

The sheath 222 may be attached at two different points to the elongated member 202, but need only be attached at one point to practice the invention. First, sheath 222 may be attached to open first end 204 at optional sheath attachment point 226 of elongated member 202. Second, the sheath 222 will be attached to elongated member 202 at sheath attachment point 228. The first point of attachment is optional because sheath 222 can be left unattached at open first end 204. Sheath attachment point 228 is generally the point wherein the material of elongated member 202 is no longer woven, which is also the beginning of pigtails 230, 232, 234. Further, at both optional sheath attachment point 226 and sheathe attachment point 228, sheaths 222 are attached only to one wall of elongated member 202. This promotes axial gripping secondary to traction and prevents interruption of ability to peel in the event the device will need to be removed before delivery of the fetus. Although sheaths 222 are depicted as extending to the openings formed by pigtails 230, 232, 234, elongated member 202 could be completely closed at second end 206, and sheaths 222 could be attached at buttonhole slits in outer layer 210.

As seen in FIG. 20, the point where elongated member 202 is no longer woven branches out into three different pigtail branches 230, 232, 234. Pigtails 230, 232, 234 are joined together at traction handle means 236. Traction handle means 236 is used to hold the pigtails 230, 232, 234 together, as well as being used as a location for the operator of the device, generally a medical doctor, to grab hold and exert a lateral pulling force thereon. As seen, traction handle means 236 is an oval shaped member, but of course may take on different shapes.

Removal ring means 238 are also provided. The ring means 238 are for quick removal of the device if necessary. One or more ring means 238 are attached only to the outer layer 210. The ring means 238 functions by allowing pulling to be done only on the outer layer 210 of elongated member 202 on one quadrant. Pulling on the ring means 238 by the operator causes elongated member 202 to peel off of the head of the fetus by destroying the axial gripping of braid material 208. The ring means 238 must be positioned on elongated member 202 such that they remain outside of the introitus for easy access after insertion of the device 200 into the birth canal.

Referring now to FIG. 21, the cephalic curve insertion wand member 250 of the preferred embodiment is illustrated. The insertion wand member 250 has a first surface 252 that in turn leads to a first curved surface 256. First curved surface 256 terminates at wand end 258. Wand end 258 can be flattened (not shown) to prevent protrusion through braid material 208 during positioning of the device. Extending from wand end 258 is second curved surface 260 which generally approximates the cephalic curve of the fetus. Second curved surface 260 extends to second surface 262, with second surface 262 concluding at the insertion wand member handle means 264. Wand end 258 must be thin enough to be pliable, yet thick enough to retain longitudinal strength.

Referring now to FIG. 22A, the preferred embodiment of braid material 208 will now be described. Depicted is flat parallel series of monofilament strands 272, such as fishing line. In the preferred embodiment, the number of monofilament strands used in each series is five but more or fewer strands could be used. Braid material 208 is constructed by loosely weaving series of strands 272 in an over and under manner as shown in FIG. 22A. Braid material 208 is distinguished from a conventionally woven material in that each Angle 1 of FIG. 22A is approximately 60 degrees and the weave is loose so that series of strands 272 are in slidable relation to one another. Although it is preferred that Angle 1 measure approximately 60 degrees, one skilled in the art could practice the invention with measures of Angle 1 greater than, or less than, 60 degrees. However, axial gripping is best demonstrated when Angle 1 is less than 90 degrees. Elongated member 202 is constructed so that a line bisecting each Angle 1 of braided material 208 is substantially aligned with the long axis of elongated member 202.

Braid material 208 may also be constructed as depicted in FIG. 22B. In this embodiment, flat, woven, shoelace type material 270 will be interwoven with flat parallel series of monofilament strands 272. This composition gives body to device 200 and adds strength to braid material 208.

Although in the embodiment depicted braid material 208 is constructed of monofilament fibers or shoelace type material, one skilled in the art could construct braid material 208 from any material or series of fibers which would allow elongated member 202 to exhibit the axial gripping discussed earlier. Finally, it should be noted that the portions of braid material 208 depicted in FIGS. 22A and B pertain to both outer layer 210 and inner layer 212.

Figure 25:
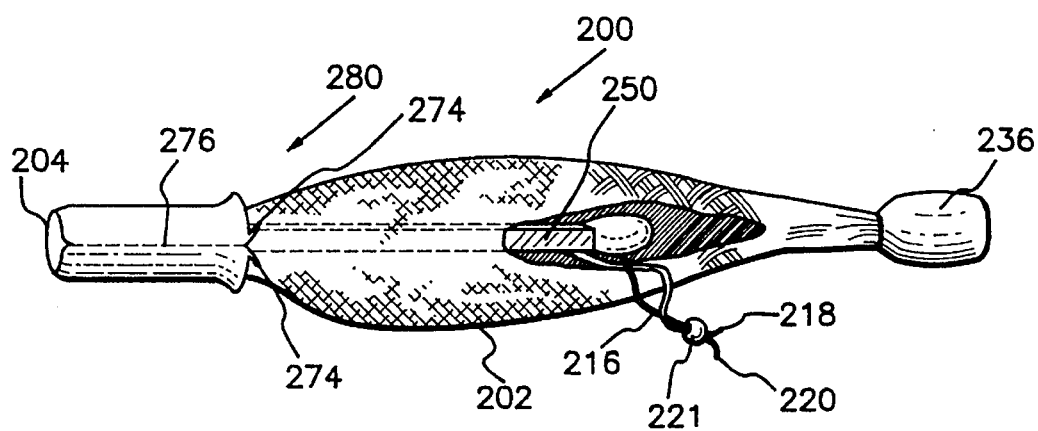
FIG. 25 is a three dimensional view of the embodiment of FIG. 20 that has contained thereon the constricting means.

Referring to FIG. 25, the preferred embodiment is depicted wherein constricting means 280 is included. The constricting means 280 is generally a cylindrical piece of clear plastic shrink wrap which is disposed about open first end 204. Constricting means 280 is included in order to constrict the diameter of open first end 204 so that the device 200 can be inserted to a sufficient depth, and then once the appropriate depth is reached, which generally is about one-half an inch into the vaginal introitus, but may vary depending on the characteristics of the mother, tabs 274 will be pulled by the operator of the device and the device will be separated along the perforated line 276. Next, constricting means 280 is removed and discarded. Since open first end 204 has been inserted to a sufficient depth, the device 200 is in place to begin positioning open first end 204 about the head of the fetus as will be more fully set out in the operation portion of the specification. FIG. 25 also depicts the insertion wand member 250 which has been inserted into the sheath member 222, as well as drawstring 216.

Figure 26:
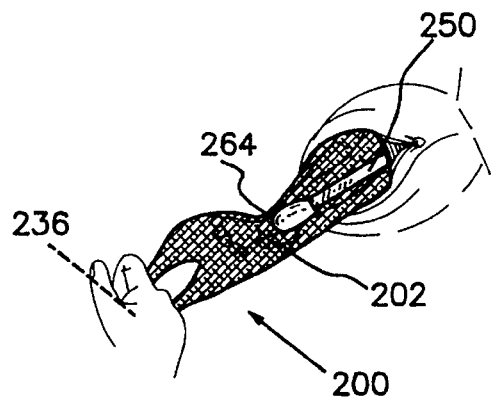
FIG. 26 is a three dimensional view of an embodiment of the invention being inserted and positioned to deliver a breech birth.
Figure 27:
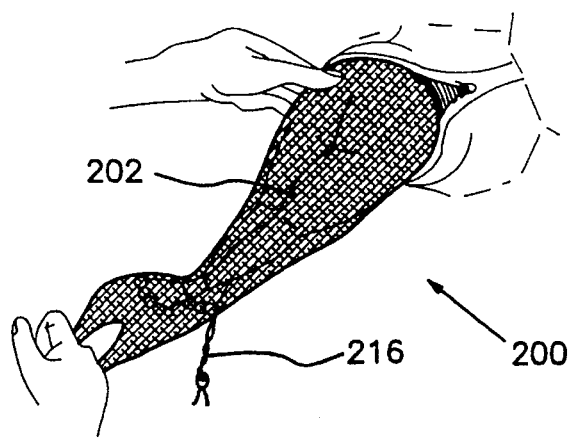
FIG. 27 is another three dimensional view of the embodiment shown in FIG. 26 being used to deliver a breech birth.

Still another embodiment of the invention is depicted in FIGS. 26 and 27 which depicts the device being utilized for breech births. FIG. 26 illustrates the device being inserted and positioned for the breech delivery. FIG. 27 represents the device being used to deliver the fetus.

In operation, the device 3, as shown in the embodiments of FIGS. 1–4, is first positioned on the top of the fetus' head 4 with the wands 27 fitted into pockets 25. The wands 27 are then maneuvered by pushing the ends of each wand 27 against the inside walls of their respective pocket 25 until the device is slipped over the head of the fetus. When the collar 7 extends posterior to the head 4 the physician then adjusts collar 7 so that it fits loosely about neck area 10, but is restricted so as not to easily slip over the head 4. The physician then grabs the end 11 and applies a pulling force which will cause the collar 7 to exert an equalized and evenly distributed resistance to the pulling force sufficient to initiate axial uniform gripping of the fetal skull in the manner of the Chinese Handcuff. This pulling force will assist the mother in natural childbirth. Once the fetus has been removed, the physician then removes device 3 from the head 4. The device is then preferably discarded and not reused.

As regards the method of assisting the delivery of an infant during childbirth utilizing the elongated member of FIG. 5 and the insertion means of FIGS. 14A and B, first, the insertion means, which comprises members 162, 164, and 166, are fitted into the pocket means 114. Then, the collar means 110 is guided over the head of the fetus by applying force to the insertion means until the collar is anteriorly below chin depth and posteriorly below the smallest portion of fetal skull as shown in FIG. 13.

Next, the device is pulled from the second end 104 of the elongated member 100, and the pulling force exerted on the second end 104 will be uniformly distributed about the head of the fetus due to the axial gripping of the mesh. Continuous or intermittent pulling, as needed, on the second end 104 will result in assistance in delivery of the fetus.

The delivery of the fetus may also be accomplished with any of the other embodiments heretofore disclosed. For instance, the insertion means 116 may be employed, instead of use of the members 162, 164, and 166, for guiding the collar means 110 over the infants head. In such a case, after the apparatus has been positioned through manipulation of the first and second members, 120 and 122, the insertion means 116 will be withdrawn as heretofore described. Also, the wand holding means 152 may also be employed, as previously described.

The operation of the preferred embodiment shown in FIG. 20 will now be described with reference to FIG. 23 which depicts a cut-away view of the fetus in the birth canal with the device 200 being placed about the head of the fetus when the fetus is in the occipital anterior position. Generally, the device 200, and in particular open first end 204, is inserted at the vaginal introitus using the cephalic curve insertion wand member 250. If deemed appropriate, two insertion wand members 250 may be employed. Constricting means 280 will be inserted to a suitable depth, which is generally about one-half inch to three-quarters of an inch, depending on the particular circumstances. After positioning open first end 204 at the proper depth, tabs 274 are pulled and the constricting means 280 is removed and discarded. Although it is preferred to use constricting means 280 to aid in the insertion of device 200, one skilled in the art could insert the device without constricting means 280 by using only insertion wand members 250.

Next, elongated member 202 is moved further into the birth canal with insertion wand members 250 enclosed between the layers 210, 212 (within the nylon sheath 222) in sequential fashion i.e. incrementally moving open first end 204 below the widest cross-section of the head of the fetus, as presented in the birth canal, allowing the device to encircle the head of the fetus. After completion of this maneuver, restricting means 215 in open first end 204 should be, optimally, enveloping the mentum of the fetus. If two sheaths 222 are utilized, two insertion wand members 250 will also be utilized, thereby allowing for incremental movement by each wand in separate movements. Although open first end 204 is optimally positioned below the mentum of the fetus' head prior to traction being applied, it is only necessary that open first end 204 be below the widest cross-section of the head of the fetus, as presented.

Referring to FIG. 24, once restricting means 215 has been properly positioned by the transmitting of force from the insertion wand end 258 to the device 200, the operator will begin to pull on drawstring 216 by grasping fastener 221 and pulling. Concurrent with this step, the operator will also continue to place a counter-force on open first end 204 using insertion wand members 250, which will ensure that restricting means 215 and open first end 204 will remain in place about the neck of the fetus. This counter-force is applied so that insertion wand end 258 keeps open first end 204 and restricting means 215 over the head of the fetus.

Once sufficient reduction of the opening at open first end 204 has taken place due to the pulling of drawstring 216, insertion wand members 250 are then removed from sheaths 222 and the operator may continue lateral pulling on traction handle means 236 so that the axial gripping forces of braid material 208 can be initiated, which in turn distributes the pulling force to all areas of elongated member 202 which have been expanded by the head of the fetus. If it is necessary to reposition the device, insertion wand members 250 are replaced into sheaths 222.

Appropriate traction should be applied at second end 206 using traction handle means 236 of the device 200. This will cause braid material 208 to axially grip the head of the fetus. Constant or intermittent traction can be applied to facilitate the head's passage through the birth canal.

The invention is also applicable for use in breech births as seen in FIGS. 26 and 27. In a breech footlet presentation, the feet of the fetus protrude from the introitus. In a breech delivery, the doctor will be pulling on the legs and then thighs as delivery progresses. Many times this results in injury to the skeletal growth plates of the lower extremity of the fetus. Thus, in anticipation of a breech birth, the device 200, and in particular elongated member 202 is simply manufactured such that the elongated member 202 is longer. This is necessary because the cylindrical member will be fitted from the feet to about the hip area as illustrated in FIGS. 26 and 27.

In a breech delivery, the method includes positioning the device 200 over the leg and thigh portion of the child by manipulation of insertion wand member 250 in sheath 222. Once sufficient penetration has occurred, the operator may begin pulling on traction handle means 236 which will initiate axial gripping on those parts of the body that have expanded elongated member 202. The operator applies continual force to open first end 204 using the insertion wand member 250.

Movement of the fetus from the womb will allow for the relaxation of the axial gripping, and it will be necessary to position open first end 204 further up the body of the fetus to above the thigh and hip. This is accomplished in the same fashion in that insertion wand members 250 are pushed sequentially upward until the appropriate depth is reached wherein pressure is maintained on open first end 204 by insertion wand members 250, drawstring 216 is tightened and elongated member 202 is pulled using traction handle means 236, thereby initiating axial gripping. Thereafter, insertion wand member 250 can be removed and pulling may continue in order to deliver the fetus.

Finally, the invention should be understood to assist in the delivery of any type of fetus, not limited to only human fetuses. In other words, the embodiments disclosed would also be applicable to veterinary obstetrics in deliveries of such mammals as horses, cattle, and sheep.

There are, of course, other alternate embodiments which are obvious from the foregoing descriptions of the invention which are intended to be included within the scope of the invention as defined by the following claims.

I claim:

1. An apparatus for assisting delivery of a fetus, comprising:

an elongated member having an open first end and a second end connected by a passageway, said elongated member constructed of braid material comprising loosely interwoven series of fibers, said series of fibers being in slidable relation with one another and said fibers being terminated at each end of said elongated member in such a manner that said elongated member will exert axial gripping forces when pulled from said second end, said open first end and said passageway sized to receive therein, and surround, the neck and the head of a fetus, said fibers being terminated at said open first end by folding said elongated member within the opening of said open first end so that said elongated member comprises a double-layer of said fibers;

a restricting means cooperating with said open first end to tighten said open first end about said neck and said head of said fetus at a location below the maximum diameter of said head as said head is presented in the birth canal in order to initiate said axial gripping forces when said elongated member is pulled from said second end; and one or more insertion means for positioning of said elongated member about said head of said fetus so that said open first end is positioned below the maximum diameter of said head as presented in the birth canal.

2. A device for assisting the delivery of a fetus, comprising:

a double-layered elongated member having an open first end and a second end connected by a passageway into which the head of a fetus may be fit, said open first end being adapted to receive said head of said fetus therein so that said open first end surrounds said head of said fetus, said elongated member having an outer layer and an inner layer formed by folding said elongated member at said open first end;

one or more sheath members, disposed along said elongated member, each said sheath member having a terminal end and a receiving end, wherein said receiving end is attached to said elongated member intermediate said open first end and said second end;

insertion means for positioning said open first end of said elongated member over said head of said fetus wherein said insertion means is adapted to be received within said receiving end of said sheath;

restricting means cooperating with said open first end of said elongated member for tightening said open first end about the neck of said head of said fetus, said restricting means comprising a drawstring having a first end and a second end, wherein said drawstring extends at least partially about said open first end of said elongated member and traverses toward said second end of said elongated member, wherein said first and second ends of said drawstring are joined together at said second end of said elongated member so that as said first and second ends of said drawstring are pulled, said open first end is tightened about said neck and said head of said fetus;

traction handle means attached to said second end of said elongated member for exerting a pulling force at said second end of said elongated member in order to initiate and maintain axial gripping of said elongated member on said head of said fetus; and one or more removal ring means, attached to said outer layer of said elongated member and adapted so that as said removal ring means is pulled, previously initiated axial gripping is reduced to permit removal of said elongated member from said head of said fetus.

3. The apparatus of claim 2 wherein said elongated member is constructed of a braid material.

4. The apparatus of claim 3 wherein said braid material comprises loosely interwoven series of monofilament strands.

5. The apparatus of claim 3 wherein said braid material comprises flat shoelace type material loosely interwoven with series of monofilament series.

6. The apparatus of claim 3, further comprising a constricting means, attachable to said open first end of said elongated member, for constricting said open first end to a size sufficient to allow insertion of said open first end into the birth canal of the mother, said constricting means being adapted so that said constricting means may be removed after said insertion of said open first end.

7. A method of assisting the delivery of a fetus during birth, the method comprising the steps of:

a) preparing an apparatus for insertion into the introitus of a mother, said apparatus including: an elongated member having an open first end and a second end connected by a passageway wherein said elongated member is constructed of braid material and adapted so that said open first end of said elongated member may receive therein, and surround, the neck and the head of a fetus; one or more sheath members attached at one end to said elongated member at a position intermediate said open first end and said second end for receiving an insertion means; one or more insertion means for positioning said open first end of said elongated member over said head of said fetus wherein said insertion means is adapted to be received within said sheath; a restricting means cooperating with said open first end for tightening said open first end about said neck and said head of said fetus; and a constricting means for allowing said open first end of said elongated member to be constricted to a diameter sufficient for insertion into the introitus of the mother;

b) inserting said elongated member into said introitus of said mother;

c) removing said constricting means so said open first end of said elongated member is allowed to expand;

d) guiding said open first end of said elongated member over said fetal head by applying force to said insertion means so that the force is transferred to said sheath member until said open first end of said elongated member is below the largest cross-section of said head of said fetus, as presented; and e) tightening said restricting means so that said open first end is fitted about said head and said neck of said fetus while continuing to apply force by said insertion means to said sheath members.

8. The method of claim 7 further comprising the steps of:

a) tightening said restriction means while pulling said apparatus at said second end so that said restricting means exerts an equalized and evenly distributed resistance to said pulling sufficient to initiate axial gripping by said braid material of said elongated member about said head of said fetus;

b) removing said insertion member from said sheath member; and c) delivery of said fetus.

9. The method of claim 8 further comprising the steps of:

a) tightening said restriction means while pulling said apparatus at said second end so that said restricting means exerts an equalized and evenly distributed resistance to said pulling sufficient to initiate axial gripping by said braid material of said elongated member about said head of said fetus;

(b) pulling on removal rings attached to said elongated member in order to interrupt said axial gripping; and (c) removing said elongated member before delivery of said fetus.

10. An apparatus for assisting the delivery of a fetus, comprising:

an elongated member having an open first end and a second end connected by a passageway;

restricting means, connected to said open first end of said elongated member, for tightening said open first end about the neck and the head of a fetus;

insertion means for positioning said open first end of said elongated member about said head of said fetus wherein said insertion means includes at least one elongated member which is capable of transmitting a force, said insertion means further comprising a first member and a second member overlaying said first member and cooperating with said first member so that said second member can be extended relative to said first member; and at least one pocket means attached to said open first end for receiving said insertion means and transmitting the force of said insertion means to said open first end so that said insertion member moves said open first end relative to said fetus, and means for providing a minimum inner diameter of said open first end capable of expanding to a diameter sufficient to permit application over the maximum diameter of said head of said fetus, as presented.

11. A device for assisting the delivery of a fetus, comprising:

an elongated member having an open first end and a second end connected by a passageway;

an elongated insertion member having a first end and a second end;

a collar means connected to said open first end of said elongated member wherein said collar means includes a means for adjusting the size of the opening at said open first end and includes at least one opening formed in said collar means for receiving said insertion member;

linear reinforcing means, connected to the first end of said elongated member, for reinforcing said elongated member; and wherein said elongated member and linear reinforcing means are constructed of a pliable material.

* * * * *